United States Patent [19]
Bennett

[11] 3,962,240
[45] June 8, 1976

[54] PROCESS FOR THE PREPARATION OF FURO(3,4-E)-AS-TRIAZINES

[75] Inventor: Gregory Benjamin Bennett, Mendham, N.J.

[73] Assignee: Sandoz, Inc., E. Hanover, N.J.

[22] Filed: May 8, 1975

[21] Appl. No.: 575,525

[52] U.S. Cl. .......................... 260/248 AS; 424/249
[51] Int. Cl.² ...................................... C07D 253/08
[58] Field of Search ............................. 260/248 AS

[56] References Cited
UNITED STATES PATENTS 3,697,518  10/1972  Schmidt et al. ...................... 260/248
3,772,276  11/1973  Sauter ................................ 260/248

Primary Examiner—John M. Ford
Attorney, Agent, or Firm—Gerald D. Sharkin; Robert S. Honor

[57] ABSTRACT

5,5,7,7-tetramethyl-3-substituted or unsubstituted-phenylfuro[3,4-e]-as-triazines, e.g., 5,7-dihydro-5,5,7,7-tetramethyl-3-(m-nitrophenyl)furo[3,4-e]-as-triazine, are prepared by reacting a 2,2,5,5-tetramethyl-3,4(2H,5H)furandione with substituted or unsubstituted benzimidic acid hydrazide under an inert atmosphere in the presence of an inert organic solvent and are useful as sleep inducers and minor tranquilizers.

10 Claims, No Drawings

PROCESS FOR THE PREPARATION OF FURO(3,4-E)-AS-TRIAZINES

This invention relates to a process for preparing 5,5,7,7-tetramethyl-3-substituted or unsubstituted phenylfuro[3,4-e]-as-triazines which are useful as sleep inducers and minor tranquilizers.

The present invention, accordingly, provides an improved process for preparing compounds of the formula:

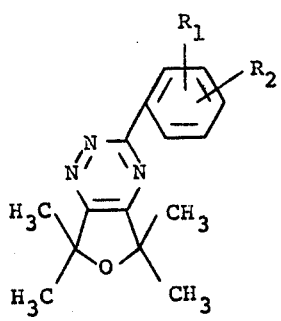 (I)

which comprises treating a compound of the formula:

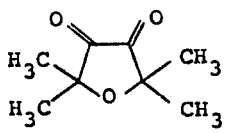 (II)

with a compound of the formula

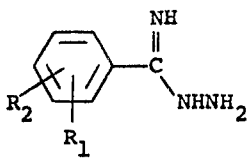 (III)

wherein
$R_1$ and $R_2$ each independently represent hydrogen, halo having an atomic weight of about 19 to 36, lower alkyl, i.e., alkyl having 1 to 4 carbon atoms, e.g., methyl, ethyl, isopropyl and the like, straight chain lower alkoxy, i.e., alkoxy having 1 to 4 carbon atoms, e.g., methoxy, ethoxy and the like, amino, nitro or trifluoromethyl, and
provided that
i. when one of $R_1$ and $R_2$ represents nitro, the other is other than nitro or trifluoromethyl;
ii. when $R_1$ and $R_2$ represent trifluoromethyl, they are on other than adjacent carbon atoms;
iii. when $R_1$ and $R_2$ represent t-butyl, they are on other than adjacent carbon atoms; and
iv. when one of $R_1$ and $R_2$ is trifluoromethyl and the other is t-butyl, they are on other than adjacent carbon atoms.

The compounds of formula (I) are prepared by treating a compound of the formula (II) with a compound of the formula (III) in the presence of an inert atmosphere, e.g., nitrogen, helium, or argon, preferably nitrogen, and in the presence of an inert, organic solvent. Although the particular solvent used is not critical, the preferred solvents include an aromatic hydrocarbon such as benzene, toluene and the like, or a lower alkanol, such as methanol, ethanol and the like, preferably ethanol. The temperature of the reaction is not critical, but it is preferred that the reaction be run from about 50° to 150°C., more preferably from about 70° to 110°C. The reaction is run from about 1 to 42 hours, preferably from about 6 to 20 hours. The product is recovered using conventional techniques, e.g., recrystallization.

Many of the compounds of formulae (II) and (III) are known and may be prepared by methods described in the literature. The compounds of formulae (II) and (III) not specifically described may be prepared from known starting materials by analogous methods.

The compounds of formula (I) are useful because they possess pharmacological activity in animals as sleep inducers and minor tranquilizers as indicated 1) by the hexobarbital reinduction method of Winter, J. Pharmacol. and Exp. Therap., 94, 7–11, 1948; 2) as indicated in the Cebus monkey using chronically implanted electrodes. Brain readings are obtained via a ten or sixteen channel electroencephalograph. For the recording sessions, the monkeys are restrained by neck and waist plates in chairs in full side observation cages at the same time every night for thirteen and one half hours Monday through Thursday. Gross behavior is monitored via closed circuit television and video tape recordings. The compound of formula (I) is administered p.o. immediately on placing the monkey in the observation cages with at least seven days intervening between drug administration. Physiological saline is administered via a similar route and at the same time on all control runs. Control data are collected at least three days per week and accumulated to give control data for fifteen sessions per monkey. Data from each session are statistically compared via computer analysis to the previous 5–15 control sessions for the particular animal, with particular emphasis given to the following phases of the sleep-wakefulness cycle: resting awake, light sleep, deep sleep, paradoxical (REM) sleep, "pseudo-"paradoxical sleep, latency to onset of deep sleep, and latency to onset of first epoch of paradoxical sleep; 3) by their ability to produce docility in behavior tests in mice given 25 to 200 mg/kg of animal body weight, i.p. of the test compound according to the 30-word adjective check sheet system basically as described by Irwin S. (Gordon Research Conference, Medicinal Chemistry, 1959) and Chen (Symposium on Sedative and Hypnotic Drugs, Williams and Wilkins, 1954); 4) by their ability to antagonize chronic convulsions and death in mice given 45 to 250 mg/kg i.p. of N-sulfamoylazepine; 5) by scoring for loss of righting reflex according to the method of Reed-Muench (American Journal of Hygiene, 27: 493–497, 1938), in which mice are administered 12.5 mg/kg, i.p. Thioridazine, immediately after which test compound is administered at dosages of 5 to 100 mg/kg in a volume of 0.1 ml/10 g. body weight. Sixty minutes after dosing, the mice are scored for loss of right reflex, and 6) by their ability to reduce conflicts as defined in the Geller Conflict Test (Irving Geller, Psychopharmacologia, Volume I, Page 42–492, 1960).

The sleep-inducing ineffective dosage of the compounds of formula (I) will vary depending on the particular compound employed. However, in general, satisfactory results are obtained when the compounds are administered orally at a daily dosage of from about 0.5 milligrams to about 100 milligrams per kilogram of animal body weight, typically given in a single dose at bedtime. For most large mammals, the total daily dosage is from about 35 to about 750 milligrams, preferably at bedtime and dosage forms suitable for internal administration comprise from about 10 to about 375 milligrams of the compound in admixture with a solid or liquid pharmaceutical carrier or diluent. The preferred pharmaceutical compositions from the standpoint of preparation and ease of administration are solid compositions, particularly hard-filled capsules and tablets.

For minor tranquilizer use, the effective dosage will vary depending on the particular compound employed. However, in general, satisfactory results are obtained when the compounds are administered orally at a daily dosage of from about 1.0 milligrams to about 200 milligrams per kilogram of animal body weight, typically given in divided doses two to four times per day. For most large mammals, the total daily dosage is from about 75 to about 1000 milligrams, and dosage forms suitable for internal administration comprise from about 18 to about 500 milligrams of the compound in admixture with a solid or liquid pharmaceutical carrier or diluent.

The compounds of formula (I) may be similarly administered in the form of their non-toxic pharmaceutically acceptable salts. Such salts possess the same order of activity as the free base and are readily prepared by reacting the base with an appropriate acid by conventional technique and, accordingly, are included within the scope of this invention. Representative of such salts are the mineral acid salts, e.g., hydrochloride, hydrobromide, sulfate and the like, and the organic acid salts such as succinate, benzoate, maleate and the like.

Tablets and capsules containing the ingredients indicated below may be prepared by conventional techniques and are useful as sleep inducers at a dose of one or two tablets just before bedtime. Tablets and capsules containing the ingredients indicated below may also be useful as minor tranquilizers in divided doses two to four times per day.

| Ingredients | Weight (mg.g) | |
|---|---|---|
| | tablet | capsule |
| 5,7-dihydro-5,5,7,7-tetramethyl-3-(m-nitrophenyl)fuoro[3,4-e]-as-triazine | 200 | 200 |
| tragacanth | 10 | — |
| lactose | 247.5 | 300 |
| corn starch | 25 | — |
| talcum | 15 | — |
| magnesium stearate | 2.5 | — |
| Total | 500 mg. | 500 mg. |

EXAMPLE 1

5,7-Dihydro-5,5,7,7-tetramethyl-3-(m-nitrophenyl)-furo[3,4-e]-as-triazine

A mixture of 1.56 g. (0.01 mole) of 2,2,5,5-tetramethyl-3,4(2H,5H) furandione and 1.80 g. (0.01 mole) 3-nitro benzimidic acid hydrazide in 100 ml. absolute ethanol is refluxed under nitrogen for 18 hours at a bath temperature of 100°C. The excess water is removed from the condensate by using a Dean Stark trap filled with 3A molecular sieves. The resulting mixture is evaporated to dryness in vacuo at 40°C., and the resulting residue is recrystallized from hexane to give 5,7-dihydro-5,5,7,7-tetramethyl-3-(m-nitrophenyl)-furo[3,4-e]-as-triazine.

Following the above procedure and using in place of 3-nitro benzimidic acid hydrazide, an equivalent amount of a. 4-chlorobenzimidic acid hydrazide,
b. 4-methylbenzimidic acid hydrazide,
c. 4-methoxybenzimidic acid hydrazide,
d. 3-trifluoromethylbenzimidic acid hydrazide,
e. 4-aminobenzimidic acid hydrazide,
f. 4-nitrobenzimidic acid hydrazide,
f. 3,5-dichlorobenzimidic acid hydrazide,
h. benzimidic acid hydrazide,
i. 3-chlorobenzimidic acid hydrazide, or
j. 4-fluorobenzimidic acid hydrazide, there is obtained a. 5,7-dihydro-5,5,7,7-tetramethyl-3-(p-chlorophenyl)-furo[3,4-e]-as-triazine,
b. 5,7-dihydro-5,5,7,7-tetramethyl-3-(p-tolyl)-furo[3,4-e]-as-triazine,
c. 5,7-dihydro-5,5,7,7-tetramethyl-3-(p-anisyl)-furo[3,4-e]-as-triazine,
d. 5,7-dihydro-5,5,7,7-tetramethyl-3-(m-trifluoromethylphenyl)-furo[3,4-e]-as-triazine,
e. 5,7-dihydro-5,5,7,7-tetramethyl-3-(p-aminophenyl)-furo[3,4-e]-as-triazine,
f. 5,7-dihydro-5,5,7,7-tetramethyl-3-(p-nitrophenyl)-furo[3,4-e]-as-triazine,
g. 5,7-dihydro-5,5,7,7-tetramethyl-3-(3',5'-dichlorophenyl)-furo[3,4-e]-as-triazine,
h. 5,7-dihydro-5,5,7,7-tetramethyl-3-phenylfuro[3,4-e]-as-triazine,
i. 5,7-dihydro-5,5,7,7-tetramethyl-3-(m-chlorophenyl)-furo[3,4-e]-as-triazine, or
j. 5,7-dihydro-5,5,7,7-tetramethyl-3-(p-fluorophenyl)-furo[3,4-e]-as-triazine, respectively.

What is claimed is:

1. A process for preparing a compound of the formula

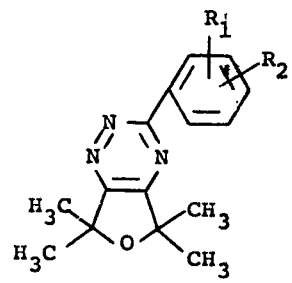

which comprises treating a compound of the formula

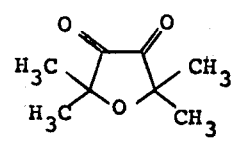

with a compound of the formula

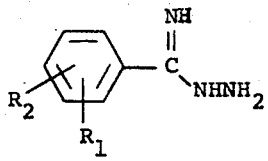

under an inert atmosphere in the presence of an inert organic solvent,
where
R₁ and R₂ each independently represent hydrogen, halo having an atomic weight of about 19 to 36, lower alkyl, straight chain lower alkoxy, amino, nitro or trifluoromethyl, and
provided that
  i. when one of R₁ and R₂ represents nitro, the other is other than nitro or trifluoromethyl;
  ii. when R₁ and R₂ represent trifluoromethyl, they are on other than adjacent carbon atoms,
  iii. when R₁ and R₂ represent t-butyl, they are on other than adjacent carbon atoms, and
  iv. when one of R₁ and R₂ is trifluoromethyl and the other is t-butyl, they are on other than adjacent carbon atoms.

2. A process according to claim 1 which is carried out at a temperature of from about 50° to 150°C.

3. A process according to claim 1 which is carried out at a temperature of from about 70° to 110°C.

4. A process according to claim 3 in which the inert organic solvent is a lower alkanol.

5. A process according to claim 2 in which the reaction is run from 1 to 42 hours.

6. A process according to claim 3 which is carried out under a nitrogen atmosphere.

7. A process according to claim 1 which is carried out under an inert atmosphere at a temperature of 70° to 110°C. in the presence of a lower alkanol.

8. A process for preparing a compound of the formula

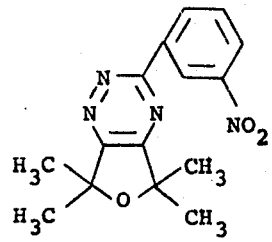

which comprises treating a compound of the formula

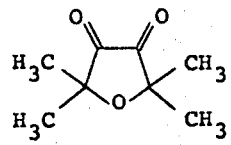

with a compound of the formula

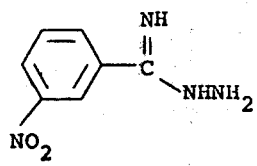

under an inert atmosphere and in the presence of an inert organic solvent at a temperature of 50° to 150°C.

9. A process according to claim 8 which is carried out at a temperature of 70° to 110°C.

10. A process according to claim 9 in which the inert organic solvent is a lower alkanol.

* * * * *